(12) United States Patent
Mohan Pinjala et al.

(10) Patent No.: US 10,709,447 B2
(45) Date of Patent: Jul. 14, 2020

(54) JAW MEMBERS AND METHODS OF MANUFACTURE

(71) Applicant: Covidien LP, Mansfield, MA (US)

(72) Inventors: Venkata Ramana Mohan Pinjala, Hyderabad (IN); Rajasekhar Nukala, Secunderabad (IN)

(73) Assignee: COVIDIEN LP, Mansfield, MA (US)

( * ) Notice: Subject to any disclaimer, the term of this patent is extended or adjusted under 35 U.S.C. 154(b) by 212 days.

(21) Appl. No.: 15/920,859

(22) Filed: Mar. 14, 2018

(65) Prior Publication Data

US 2018/0199938 A1    Jul. 19, 2018

Related U.S. Application Data

(62) Division of application No. 14/503,481, filed on Oct. 1, 2014, now Pat. No. 9,924,943.

(51) Int. Cl.
*A61B 17/00* (2006.01)
*A61B 17/072* (2006.01)
(Continued)

(52) U.S. Cl.
CPC ...... *A61B 17/072* (2013.01); *A61B 17/07207* (2013.01); *B21D 35/005* (2013.01);
(Continued)

(58) Field of Classification Search
CPC ...... A61B 2017/07271; A61B 17/0644; A61B 17/068; A61B 17/072; A61B 17/07207;
(Continued)

(56) References Cited

U.S. PATENT DOCUMENTS 1,295,769 A    2/1919   Kux
1,356,567 A  * 10/1920  Smith .................. B21D 11/08
                                                    72/379.2
(Continued)

FOREIGN PATENT DOCUMENTS

EP    1785102 A2    5/2007
EP    2165662 A1    3/2010
(Continued)

OTHER PUBLICATIONS

European Search Report dated Feb. 4, 2016, corresponding to European Application No. 15187549.9; 10 pages.
(Continued)

*Primary Examiner* — Thanh K Truong
*Assistant Examiner* — Patrick B Fry
(74) *Attorney, Agent, or Firm* — Carter, DeLuca & Farrell LLP

(57) ABSTRACT

A jaw member for use on a surgical stapling instrument includes a cartridge assembly and a cartridge housing each having an arcuate configuration. The cartridge assembly includes a surface configured to engage tissue and a plurality of rows of fastener retaining slots extending along a length of the cartridge assembly. The cartridge housing defines a channel configured for receipt of the cartridge assembly. The cartridge housing includes a base portion and a plurality of tabs. The base portion has a concave inner edge and a convex outer edge. The tabs extend from the concave inner edge and the convex outer edge. The tabs are spaced from one another along a length of the cartridge housing.

20 Claims, 4 Drawing Sheets

(51) Int. Cl.
  *B21D 35/00* (2006.01)
  *B23P 19/10* (2006.01)
(52) U.S. Cl.
  CPC ..... *B23P 19/10* (2013.01); *A61B 2017/00477* (2013.01); *A61B 2017/00526* (2013.01); *A61B 2017/07214* (2013.01); *A61B 2017/07221* (2013.01); *A61B 2017/07271* (2013.01); *A61B 2017/07285* (2013.01)
(58) Field of Classification Search
  CPC ........... A61B 2017/07214; A61B 2017/07278; A61B 17/1155; B21D 13/02; B21D 11/08; B21D 7/021; B21D 11/085; B21D 11/20; B21B 5/16
  USPC ............... 72/379.2; 227/175.1, 176.1, 180.1; 428/575
  See application file for complete search history.

(56) References Cited

U.S. PATENT DOCUMENTS

| | | | |
|---|---|---|---|
| 2,190,004 A | 2/1940 | Baker | |
| 2,224,338 A | 12/1940 | Bowers | |
| 2,560,786 A | 7/1951 | Wright et al. | |
| 4,215,194 A | 7/1980 | Shepherd | |
| 5,083,449 A | 1/1992 | Kobayashi et al. | |
| 5,100,042 A | 3/1992 | Gravener et al. | |
| 6,012,494 A * | 1/2000 | Balazs | B25J 18/06 138/110 |
| 6,412,325 B1 | 7/2002 | Croswell | |
| 6,640,605 B2 | 11/2003 | Gitlin et al. | |
| 7,328,829 B2 | 2/2008 | Arad et al. | |
| 7,651,017 B2 * | 1/2010 | Ortiz | A61B 17/064 227/176.1 |
| 7,685,857 B2 * | 3/2010 | MacDonald-Schmidt | B21C 23/002 72/256 |
| 7,891,531 B1 * | 2/2011 | Ward | A61B 17/07207 227/156 |
| 8,215,532 B2 | 7/2012 | Marczyk | |
| 8,360,298 B2 | 1/2013 | Farascioni et al. | |
| 8,459,521 B2 | 6/2013 | Zemlok et al. | |
| 8,740,039 B2 * | 6/2014 | Farascioni | A61B 17/07207 227/175.1 |
| 9,345,480 B2 * | 5/2016 | Hessler | A61B 17/068 |
| 9,924,943 B2 | 3/2018 | Mohan Pinjala et al. | |
| 2001/0037571 A1 * | 11/2001 | Horng | B21D 53/04 29/890.03 |
| 2004/0092373 A1 | 5/2004 | Petersen | |
| 2007/0114261 A1 | 5/2007 | Ortiz et al. | |
| 2008/0041916 A1 | 2/2008 | Milliman et al. | |
| 2008/0105730 A1 | 5/2008 | Racenet et al. | |
| 2008/0110960 A1 | 5/2008 | Jankowski | |
| 2008/0142565 A1 | 6/2008 | Ehrenfels et al. | |
| 2009/0272785 A1 | 11/2009 | Sonnenschein et al. | |
| 2010/0072258 A1 | 3/2010 | Farascioni et al. | |
| 2011/0087259 A1 | 4/2011 | Marczyk | |
| 2011/0163150 A1 * | 7/2011 | Farascioni | A61B 17/07207 227/181.1 |
| 2012/0080498 A1 | 4/2012 | Shelton, IV et al. | |
| 2013/0206816 A1 | 8/2013 | Penna | |
| 2014/0158741 A1 | 6/2014 | Woodard, Jr. et al. | |
| 2014/0203063 A1 * | 7/2014 | Hessler | A61B 17/068 227/176.1 |
| 2014/0224686 A1 | 8/2014 | Aronhalt et al. | |

FOREIGN PATENT DOCUMENTS

| | | |
|---|---|---|
| EP | 2732772 A1 | 5/2014 |
| WO | 0191646 A1 | 12/2001 |

OTHER PUBLICATIONS

"Steel Rule Dies", Machinery's Handbook, 26th Ed. Oberg, et al., 2000; pp. 1315-1317.
European Communication dated Jun. 28, 2017, corresponding to European Application No. 15187549.9; 4 pages.

* cited by examiner

JAW MEMBERS AND METHODS OF MANUFACTURE

CROSS-REFERENCE TO RELATED APPLICATION

This application is a divisional application of U.S. patent application Ser. No. 14/503,481, filed on Oct. 1, 2014, the entire contents of which are incorporated by reference herein.

BACKGROUND

Technical Field

The present disclosure relates generally to surgical instruments and, more specifically, to surgical instruments for surgically joining tissue and methods of manufacturing jaw members of the surgical instruments.

Background of Related Art

Surgical stapling instruments used for applying parallel rows of staples through compressed living tissue are well known in the art. These surgical instruments are commonly employed for closing tissue or organs prior to transaction or resection, for occluding organs in thoracic and abdominal procedures, and for fastening tissue in anastomoses.

Typically, such surgical stapling instruments include an anvil assembly, a cartridge assembly for supporting an array of surgical staples, an approximation mechanism for approximating the anvil and cartridge assemblies, and a firing mechanism for ejecting the surgical staples from the cartridge assembly.

In use, a surgeon initially approximates the anvil and cartridge assemblies. Next, the surgeon can actuate the surgical instrument to place staples in tissue. Additionally, the surgeon may use the same surgical instrument or a separate instrument to cut the tissue adjacent or between the row(s) of staples. Alternatively, the surgical instrument can sequentially eject the staples while the anvil and cartridge assemblies are approximated.

SUMMARY

In one embodiment, the present disclosure relates to a jaw member for use with a surgical instrument for surgically joining tissue. The jaw member includes a cartridge assembly and a cartridge housing each having an arcuate configuration. The cartridge assembly includes a surface configured to engage tissue, a plurality of rows of fastener retaining slots extending along a length of the cartridge assembly, and a knife channel disposed between adjacent rows of the plurality of rows of fastener retaining slots. The cartridge housing defines a channel therein configured for receipt of the cartridge assembly. The cartridge housing includes a base portion having a concave inner edge and a convex outer edge. A plurality of tabs extend from the concave inner edge and the convex outer edge. The tabs are spaced from one another along a length of the cartridge housing.

In embodiments, the cartridge assembly may have an inner concave edge and an outer convex edge. The inner concave edge or the outer convex edge of the cartridge assembly may have a protrusion. The tabs that extend from the inner or outer edge of the cartridge housing may define a hole therethrough configured for receipt of respective protrusions on the inner or outer edge of the cartridge assembly. The protrusion may be configured for snap fit engagement with the hole.

In embodiments, the cartridge housing may be fabricated from sheet metal.

In embodiments, the concave inner edge and the convex outer edge of the base portion may define a plurality of notches.

In another aspect of the present disclosure, a jaw member for use with a surgical stapling instrument is provided. The jaw member includes a cartridge assembly and a cartridge housing each having an arcuate configuration. The cartridge assembly includes a surface configured to engage tissue, a plurality of rows of fastener retaining slots extending along a length of the cartridge assembly, and a knife channel disposed between adjacent rows of the plurality of rows of fastener retaining slots. The cartridge housing defines a channel therein configured for receipt of the cartridge assembly. The cartridge housing includes a base portion, a first wall, and a second wall. The base portion has a concave inner edge and a convex outer edge. The first wall extends from the concave inner edge. The second wall extends from the convex outer edge. The first and second walls each define a plurality of slits. The slits are spaced from one another along a length of the cartridge housing.

In embodiments, the first wall of the cartridge housing may have a top surface and a bottom surface and the second wall of the cartridge housing may have a top surface and a bottom surface. Each slit may extend from the top surface of one of the first wall or the second wall to the bottom surface of one of the first wall or the second wall.

In embodiments, the cartridge assembly may have a concave inner edge and a convex outer edge. The concave inner edge or the convex outer edge of the cartridge assembly may have a protrusion. The first wall or the second wall of the cartridge housing may define a hole therethrough configured for receipt of the protrusion of the cartridge assembly.

In yet another aspect of the present disclosure, an end effector for use with a surgical stapling instrument is provided. The end effector includes a first jaw member having an anvil assembly and a second jaw member. The jaw members are movable relative to one another between a spaced position and an approximated position to engage and staple tissue therebetween. The second jaw member includes a cartridge assembly and a cartridge housing each having an arcuate configuration. The cartridge assembly includes a surface configured to engage tissue, a plurality of rows of fastener retaining slots extending along a length of the cartridge assembly, and a knife channel disposed between adjacent rows of the plurality of rows of fastener retaining slots. The cartridge housing defines a channel therein configured for receipt of the cartridge assembly. The cartridge housing includes a base portion, a first wall, and a second wall. The base portion has a concave inner edge and a convex outer edge. The first wall extends from the concave inner edge. The second wall extends from the convex outer edge. The first and second walls each define a plurality of slits. The slits are spaced from another along a length of the cartridge housing.

In yet another aspect of the present disclosure, a method of manufacturing a jaw member of a surgical stapling instrument is provided. The method includes providing a piece of sheet metal having an elongated configuration. A plurality of slits are formed in the piece of sheet metal. A hole is formed through the piece of sheet metal. The piece of sheet metal is deformed into an arcuate shape to form a base portion, a first wall, and a second wall. The first and second walls have the plurality of slits that extend from the base portion. The base portion, the first wall, and the second wall together define a channel along a length of the piece of sheet metal. A cartridge assembly is inserted into the channel of the piece of sheet metal to assemble the jaw member.

In embodiments, deforming the piece of sheet metal into an arcuate shape may include bending the piece of sheet metal such that slits disposed on the first wall contract and slits disposed on the second wall expand.

In embodiments, inserting the cartridge assembly into the channel of the piece of sheet metal may include snap fitting the protrusion of the cartridge assembly into the hole of the cartridge housing.

BRIEF DESCRIPTION OF FIGURES

Various embodiments of the presently disclosed surgical instrument are disclosed herein with reference to the drawings, wherein.

DETAILED DESCRIPTION

Figure 1:
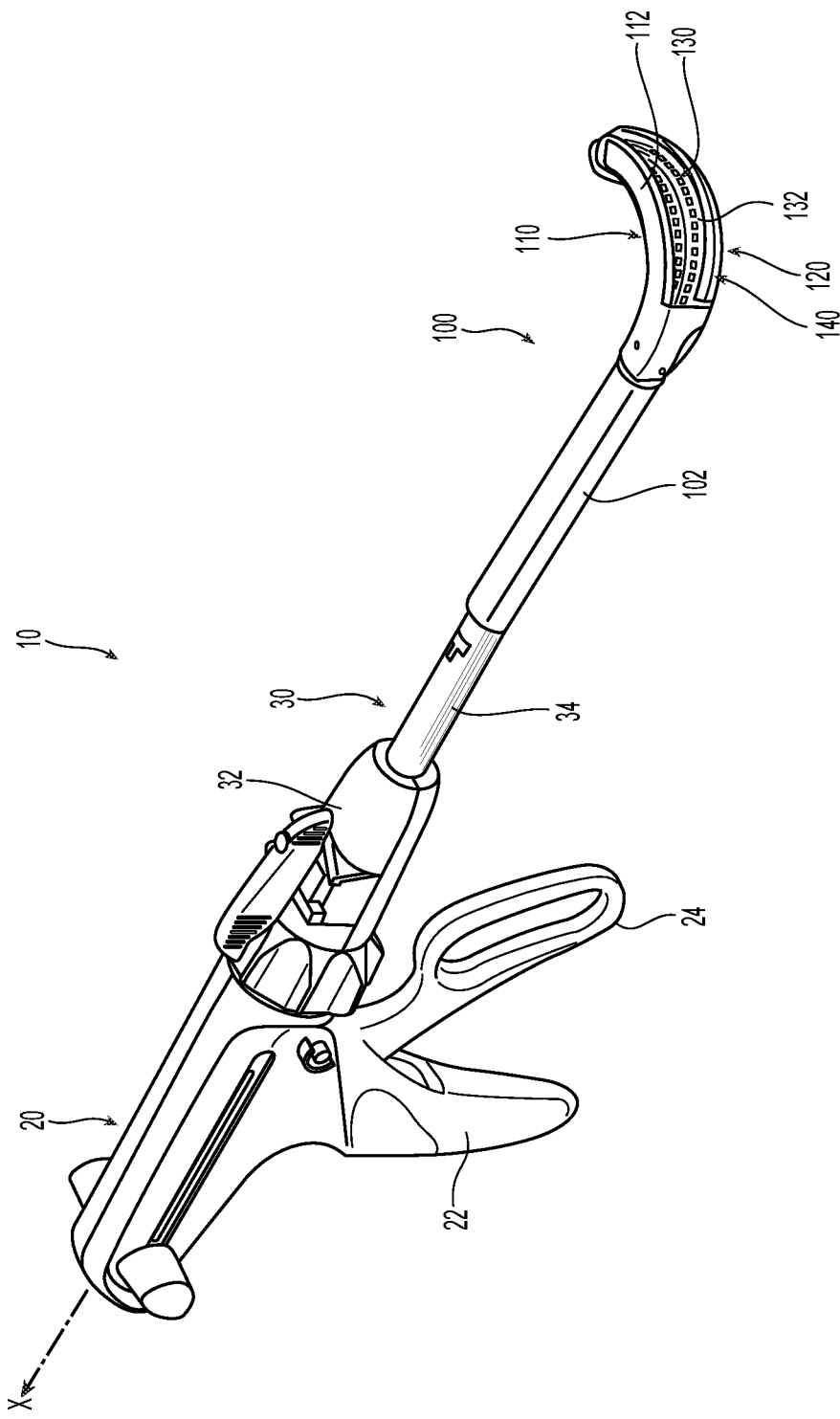
FIG. 1 is a perspective view of a surgical instrument of the present disclosure.

Embodiments of the presently disclosed surgical instrument are described in detail with reference to the drawings, wherein like reference numerals designate similar or identical elements in each of the several views. In the drawings and the description that follows, the term "proximal" refers to the end of the surgical instrument, or component thereof, that is closest to the operator, whereas the term "distal" refers to the end of the surgical instrument, or component thereof, that is farthest from the operator. As appreciated by one skilled in the art, the depicted surgical instrument fires staples, but it may be adapted to fire any other suitable fastener such as clips and two-part fasteners.

As used herein, the terms parallel and perpendicular are understood to include relative configurations that are substantially parallel and substantially perpendicular up to about +/−10 degrees from true parallel and true perpendicular.

With reference to FIG. 1, reference numeral 10 designates an embodiment of the presently disclosed surgical instrument. In the interest of brevity, the present disclosure focuses on jaw members 110, 120 of an end effector 100 of surgical instrument 10 and, more specifically, a cartridge housing 140 of jaw member 120 of surgical instrument 10. U.S. Pat. No. 8,033,442, filed on Nov. 28, 2007; U.S. Pat. No. 8,393,513, filed on Jan. 8, 2008; U.S. Pat. No. 7,568,604, filed on Jan. 24, 2008; and U.S. Pat. No. 7,565,993, filed on Oct. 15, 2007 describe in detail the structure and operation of other surgical fastening assemblies. The entire contents of these applications are hereby incorporated by reference herein.

Surgical instrument 10 is configured to clamp, fasten, and/or cut tissue. In general, surgical instrument 10 includes a handle assembly 20, an adapter assembly 30 extending distally from handle assembly 20 and defining a longitudinal axis "X," and a curved end effector 100 adapted to clamp and fasten tissue. Adapter assembly 30 interconnects handle assembly 20 and end effector 100. Adapter assembly 30 includes a proximal housing 32 operatively coupled to a distal end of handle assembly 20 and a distal elongate portion 34 operatively coupled to a proximal elongate portion 102 of end effector 100.

Handle assembly 20 includes a stationary handle 22 and a movable handle 24. Movable handle 24 is adapted to move pivotally toward or away from stationary handle 22. Further, movable handle 24 is operatively coupled to end effector 100 through a mechanism adapted to convert at least a partial actuation of movable handle 24 into a pivoting motion of at least one of a cartridge assembly 130 of second jaw member 120 or an anvil assembly 112 of first jaw member 110 between spaced and approximated positions. As recognized by one skilled in the art, any conventional actuation mechanism may be employed to operatively couple movable handle 24 to end effector 100.

In disclosed embodiments, handle assembly 20 contains an actuation mechanism for deploying fasteners, such as, for example, surgical staples from end effector 100 and advancing a knife (not shown) of end effector 100. This actuation mechanism includes a firing rod (not shown) operatively connected to movable handle 24. In operation, pivoting movable handle 24 toward stationary handle 22 causes the firing rod to advance distally. The firing rod is in turn operatively coupled to an axial drive assembly (not shown) at least partially positioned within end effector 100. The axial drive assembly is configured to move distally in response to a distal translation of the firing rod. Distal translation of the axial drive assembly causes first jaw member 110 to pivot toward second jaw member 120. In addition, the axial drive assembly pushes an actuation sled (not shown) disposed within second jaw member 120, while the actuation sled translates through end effector 100. As the actuation sled advances through second jaw member 120, this actuation sled urges fasteners out of fastener retaining slots 134 defined in second jaw member 120. In one embodiment, the axial drive assembly includes a blade (not shown) mounted on a distal portion thereof. In operation, this blade moves through end effector 100 when axial drive assembly moves distally through end effector 100.

Figure 2:
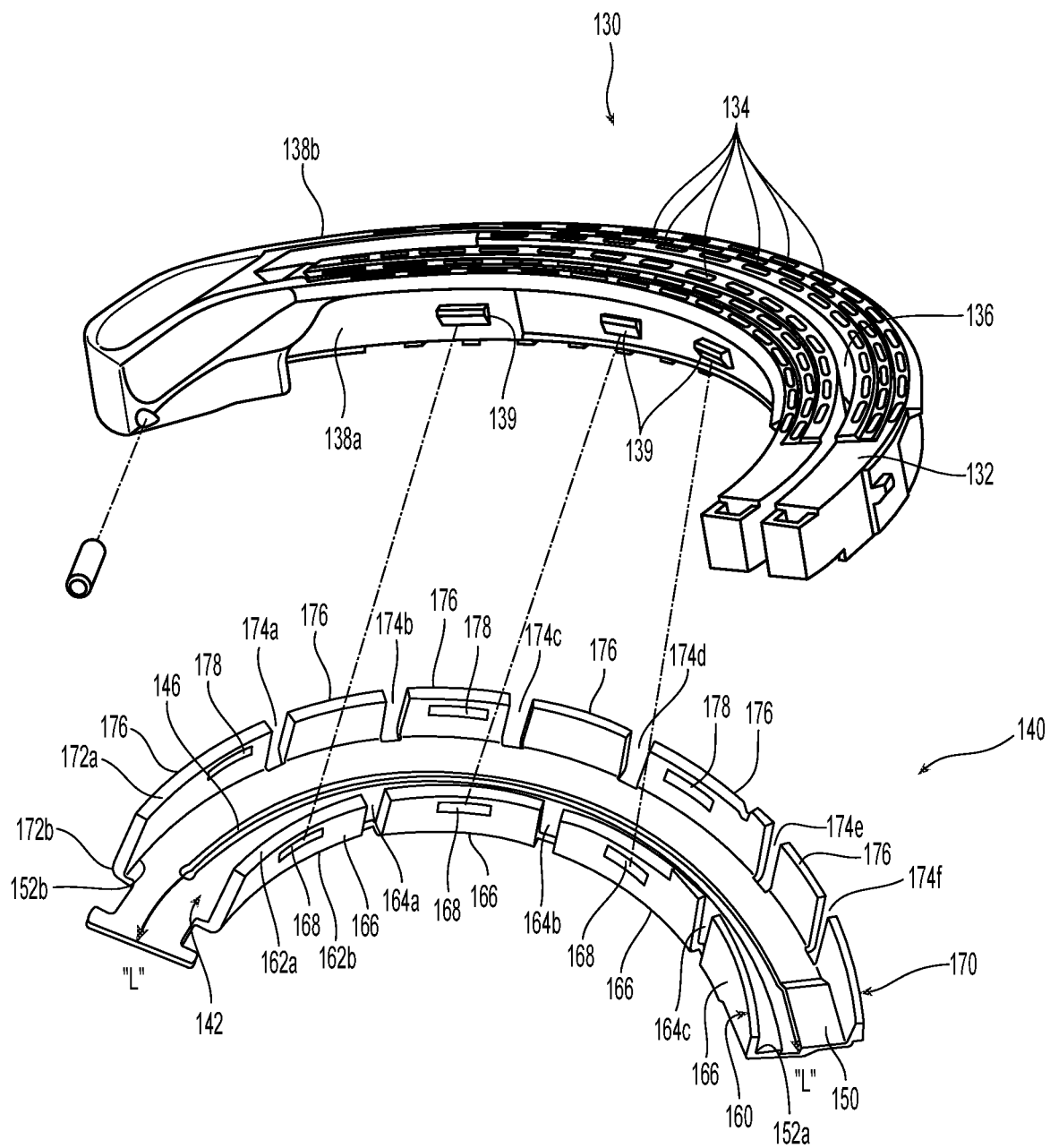
FIG. 2 is a perspective view, with parts separated, of a cartridge assembly and a cartridge housing of a jaw member of the surgical instrument shown in FIG. 1.

With reference to FIGS. 1 and 2, end effector 100 includes proximal elongate portion 102, first jaw member 110, and second jaw member 120. First and second jaw members 110, 120 have an arcuate shape (i.e., first and second jaw members 110, 120 are curved with respect to longitudinal axis "X"). It is envisioned that first and second jaw members 110, 120 may facilitate performing certain types of surgical procedures. For example, first and second jaw members 110, 120, as compared to straight jaw members, may help facilitate access to lower pelvic regions, e.g., during lower anterior resection ("LAR") or other colo-rectal surgery. First and second jaw members 110, 120 are movable, e.g., pivotable, relative to one another between a spaced-apart position and an approximated position to engage and staple tissue therebetween.

First jaw member 110 includes an anvil assembly 112 against which staples are formed during actuation of end effector 100. Second jaw member 120 includes cartridge assembly 130 and a cartridge housing 140 configured to support cartridge assembly 130 therein. Cartridge assembly 130 has an arcuate configuration and includes a surface 132 configured to engage tissue. Surface 132 of cartridge assembly 130 generally faces anvil assembly 112 (see FIG. 1) and, during operation, engages tissue when anvil assembly 112 is approximated with cartridge assembly 130.

Figure 3A:
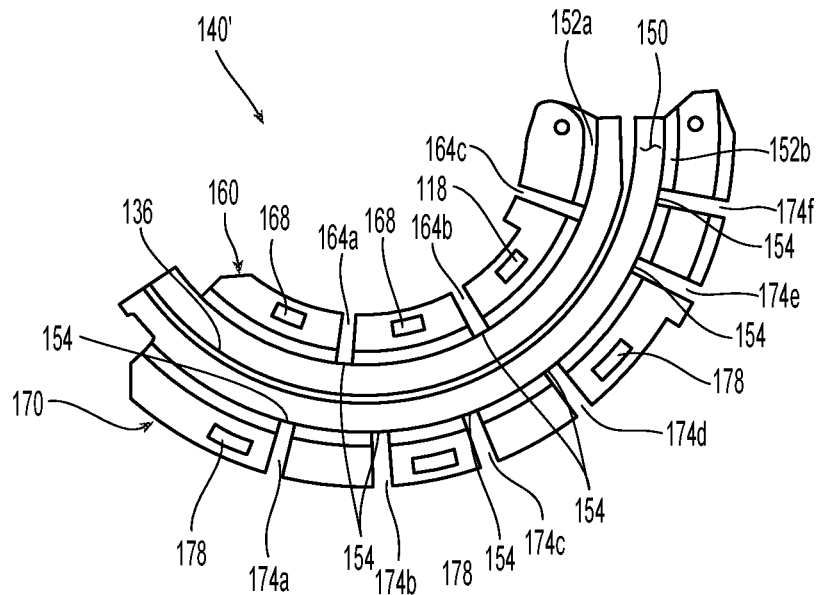
FIG. 3A is a top plan view of a piece of sheet metal to be formed into the cartridge housing shown in FIG. 2.
Figure 3B:
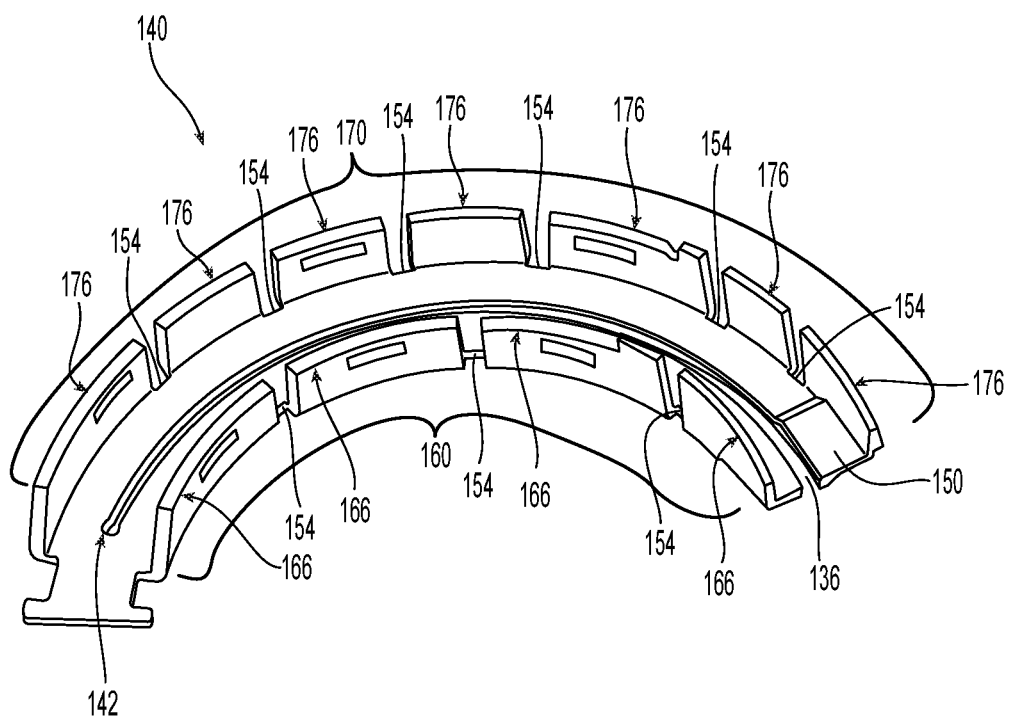
FIG. 3B is a perspective view of the piece of sheet metal of FIG. 3A after it has been formed into the cartridge housing of FIG. 2.

With reference to FIGS. 2, 3A, and 3B, cartridge assembly 130 includes a plurality of fastener retaining slots 134 defined in surface 132 of cartridge assembly 130. Fastener retaining slots 136 are arranged in arcuate rows (e.g., six concentric rows) along surface 132 and extend along a curved length of cartridge assembly 130. Each fastener retaining slot 134 is adapted to hold a fastener (not shown) until a user actuates handle assembly 20 (see FIG. 1). As mentioned above, when movable handle 24 is pivoted toward stationary handle 22, the fasteners are ejected from fastener retaining slots 134 and move toward anvil assembly 112.

Cartridge assembly 130 further includes a knife channel 136 defined in surface 132 and configured for translatable passage therethrough of a knife or other suitable cutting tool (not shown). Knife channel 136 is disposed between adjacent rows of fastener retainer slots 134 (e.g., between a third and a fourth row) and extends along the curved length of cartridge assembly 130. In operation, a knife (not shown) slides through knife channel 136 when movable handle 24 (see FIG. 1) pivots toward stationary handle 22 (see FIG. 1). Alternately, other mechanisms can be used to drive the knife through knife channel 136. As mentioned above, actuating handle assembly 20 not only drives a knife along knife channel 136 to cut tissue disposed between anvil assembly 112 and cartridge assembly 130, but also ejects the fasteners from fastener retaining slots 134 (e.g., via a single stroke or multiple strokes of movable handle 24) into the tissue.

Cartridge assembly 130 further includes an inner concave edge 138a and an outer convex edge 138b each extending along the curved length of cartridge assembly 130 and defining a width of cartridge assembly 130 therebetween. Inner concave edge 138a and outer convex edge 138b have protrusions 139 extending therefrom configured for engagement with correspondingly shaped holes 168, 178 of cartridge housing 140 to retain cartridge assembly 130 with cartridge housing 140, as described in greater detail below. Protrusions 139 have a tapered configuration to facilitate insertion of protrusions 139 into holes 168, 178 of cartridge housing 140 and to prevent removal of protrusions 139 from holes 168, 178 of cartridge housing 140 after assembly of second jaw member 120. In some embodiments, protrusions 139 may be variously configured, such as, for example, rounded, triangular, squared, polygonal, uniform, non-uniform, and/or undulating.

With continued reference to FIGS. 2, 3A and 3B, cartridge housing 140 is fabricated from sheet metal formed to define a channel 142 therein configured for receipt and retention of cartridge assembly 130. Cartridge housing 140 is coupled to proximal elongate portion 102 of end effector 100 (see FIG. 1). Cartridge housing 140 includes a base portion 150, a first wall 160, and a second wall 170. Base portion 150 is substantially planar and curved along its length. Base portion 150 includes a concave inner edge 152a and a convex outer edge 152b each extending along a curved length "L" of cartridge housing 140. A knife slot 146 configured for slidable receipt of the knife (not shown) is defined along the curved length "L" of cartridge housing 140 and disposed at a midpoint between concave inner edge 152a and convex outer edge 152b of base portion 150.

First wall 160 of cartridge housing 140 extends substantially along the entirety of the curved length "L" of cartridge housing 140 and extends from concave inner edge 152a of base portion 150. Second wall 170 of cartridge housing 140 extends substantially along the entirety of the curved length "L" of base portion 150 and extends from convex outer edge 152b of base portion 150. In embodiments, first and second walls 160, 170 extend perpendicularly from base portion 150. First wall 160 is concave relative to longitudinal axis "X" and second wall 170 is convex relative to longitudinal axis "X." First wall 160 has a top surface 162a distanced from and in parallel relation with base portion 150 and a bottom surface 162b coplanar with base portion 150. Second wall 170 also has a top surface 172a distanced from and in parallel relation with base portion 150 and a bottom surface 172b coplanar with base portion 150.

First and second walls 160, 170 each define a plurality of slits 164a-c, 174a-f, respectively, therein that are spaced from one another along the curved length "L" of cartridge housing 140. In the illustrative embodiment shown in FIG. 2, each slit 164a-c, 174a-f extends from top surface 162a, 172a of respective first wall 160 and second wall 170 and through bottom surface 162b, 172b of respective first wall 160 and second wall 170 such that first and second walls 160, 170 are segmented into a plurality of tabs 166, 176. Each slit 164a-c, 174a-f also extends through base portion 150 to define a plurality of notches 154 (see FIGS. 3A and 3B) formed in inner concave edge 152a and outer convex edge 152b of base portion 150. Notches 154 are spaced along the curved length "L" of cartridge housing 140. In some embodiments, slits 164a-c, 174a-f may be spaced uniformly or non-uniformly along the curved length "L" of cartridge housing 140.

Slits 164a-c, 174a-f assist in bending cartridge housing 140 into a selected curvature and overall shape by providing relief points at which cartridge housing 140 will bend upon an application of bending forces, as described in greater detail below. Slits 164a-c, 174a-f may be variously shaped and have various dimensions depending on the desired curvature and/or overall shape of cartridge housing 140. For example, if cartridge housing 140 is to accommodate a cartridge assembly of an increased curvature (i.e., smaller diameter), slits 164a-c, 174a-f may have an increased width (i.e., tabs 166, 176 will be spaced further apart) or more slits may be formed in cartridge housing 140. Slits 164a-c, 174a-f also assist in the extrusion of the cartridge housing 140 during formation of cartridge housing 140.

First and second walls 160, 170 further define a plurality of holes 168, 178 therethrough configured for receipt of respective protrusions 139 of cartridge assembly 130 therein. In some embodiments, some or all of tabs 166, 176 define a hole 168, 178 therethrough.

Figure 4:
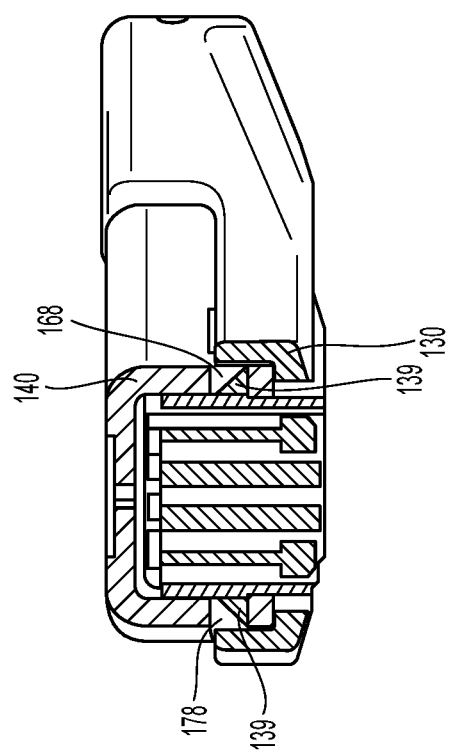
FIG. 4 is a cross sectional view of the assembled cartridge assembly and cartridge housing.

With reference to FIGS. 3A, 3B, and 4, a method of manufacturing jaw member 120 will be described. A piece of sheet metal 140' is provided having an elongated configuration. Slits 164a-c, 174a-f are formed transversely through lateral edges of the piece of sheet metal 140'. Holes 168, 178 are formed through the piece of sheet metal 140'. The piece of sheet metal 140' is deformed into an arcuate shape, as shown in FIG. 3A, by bending the piece of sheet metal 140' such that slits 164a-c formed in first wall 160 contract and slits 174a-f formed in second wall 170 expand. As mentioned above, slits 164a-c, 174a-f assist in bending the piece of sheet metal 140' into an arcuate shape by providing relief points at which bending is more easily effected.

First wall 160 and second wall 170 are bent inwardly towards one another about inner concave edge 152a and outer convex edge 152b of base portion 150. Slits 164a-c, 174a-f also assist in bending first and second walls 160, 170 relative to base portion 150. It is contemplated that inner concave edge 152a and outer convex edge 152b of base portion 150 are thinner than the remainder of base portion 150 (e.g., depressions are formed therein) such that bending of first wall 160 and second wall 170 is predisposed to occur at inner concave edge 152a and outer convex edge 152b of base portion 150 upon application of a bending force thereto. First and second walls 160, 170 are bent relative to base portion 150 until first and second walls 160, 170 extend substantially perpendicularly from base portion 150 to define channel 142 dimensioned for receipt of cartridge assembly 130 as shown in FIG. 3B.

Cartridge assembly 130 is inserted into channel 142 of the piece of sheet metal 140', which is now in the form of cartridge housing 140, to form second jaw member 120. During insertion of cartridge assembly 130 into channel 142 of cartridge housing 140, protrusions 139 of cartridge assembly 130 snap fittingly engage holes 168, 178 defined in cartridge housing 140, as shown in FIG. 4. Cartridge housing 140, with cartridge assembly 130 retained therein, may then be coupled to the remainder of end effector 100.

It will be understood that various modifications may be made to the embodiments of the presently disclosed surgical instruments. Therefore, the above description should not be construed as limiting, but merely as exemplifications of embodiments. Those skilled in the art will envision other modifications within the scope and spirit of the present disclosure.

What is claimed is:

1. A jaw member for use on a surgical stapling instrument, the jaw member comprising:
    a cartridge assembly having an arcuate configuration, the cartridge assembly including:
        a surface configured to engage tissue;
        a plurality of rows of fastener retaining slots extending along a length of the cartridge assembly; and
        a knife channel disposed between adjacent rows of the plurality of rows of fastener retaining slots; and
    a cartridge housing having an arcuate configuration and defining a channel therein configured for receipt of the cartridge assembly, the cartridge housing including:
        a base portion having a concave inner edge and a convex outer edge; and
        a plurality of tabs extending from the concave inner edge and the convex outer edge, wherein each tab of the plurality of tabs is spaced from one another along a length of the cartridge housing.

2. The jaw member according to claim 1, wherein the cartridge assembly has an inner concave edge and an outer convex edge, at least one of the inner concave edge or the outer convex edge of the cartridge assembly has at least one protrusion, and at least one tab of the plurality of tabs defines at least one hole therethrough configured for receipt of the at least one protrusion.

3. The jaw member according to claim 2, wherein the at least one protrusion is configured for snap fit engagement with the at least one hole.

4. The jaw member according to claim 1, wherein the cartridge housing is fabricated from sheet metal.

5. The jaw member according to claim 1, wherein the concave inner edge and the convex outer edge of the base portion defines a plurality of notches therein.

6. The jaw member according to claim 1, wherein adjacent tabs of the plurality of tabs that extend from the concave inner edge are spaced from one another along the length of the cartridge housing a first distance, and adjacent tabs of the plurality of tabs that extend from the convex outer edge are spaced from one another along the length of the cartridge housing a second distance, greater than the first distance.

7. A jaw member for use with a surgical stapling instrument, the jaw member comprising:
    a cartridge assembly having an arcuate configuration, the cartridge assembly including:
        a surface configured to engage tissue;
        a plurality of rows of fastener retaining slots extending along a length of the cartridge assembly; and
        a knife channel disposed between adjacent rows of the plurality of rows of fastener retaining slots; and
    a cartridge housing having an arcuate configuration and defining a channel therein configured for receipt of the cartridge assembly, the cartridge housing including:
        a base portion having a concave inner edge and a convex outer edge;
        a first wall extending from the concave inner edge; and
        a second wall extending from the convex outer edge, the first and second walls each defining a plurality of slits therein, wherein each slit of the plurality of slits is spaced from one another along a length of the cartridge housing.

8. The jaw member according to claim 7, wherein the first wall has a top surface and a bottom surface and the second wall has a top surface and a bottom surface, wherein each slit of the plurality of slits extends from the top surface of one of the first wall or the second wall to the bottom surface of one of the first wall or the second wall.

9. The jaw member according to claim 7, wherein the concave inner edge and the convex outer edge of the base portion defines a plurality of notches therein.

10. The jaw member according to claim 7, wherein the cartridge assembly has a concave inner edge and a convex outer edge, at least one of the concave inner edge or the convex outer edge of the cartridge assembly has at least one protrusion, and at least one of the first wall or the second wall defines at least one hole therethrough configured for receipt of the at least one protrusion.

11. The jaw member according to claim 10, wherein the at least one protrusion is configured for snap fit engagement with the at least one hole.

12. The jaw member according to claim 7, wherein the cartridge housing is fabricated from sheet metal.

13. The jaw member according to claim 7, wherein the plurality of slits in the first wall have a lesser width than the plurality of slits in the second wall.

14. The jaw member according to claim 7, wherein the convex outer edge and the concave inner edge are thinner than a remainder of the base portion.

15. An end effector for use with a surgical stapling instrument, the end effector comprising:
    a first jaw member having an anvil assembly; and
    a second jaw member, at least one of the first jaw member and the second jaw member being movable relative to the other between a spaced position and an approximated position to engage and staple tissue therebetween, the second jaw member including:
        a cartridge assembly having an arcuate configuration, the cartridge assembly including:
            a surface configured to engage tissue;
            a plurality of rows of fastener retaining slots extending along a length of the cartridge assembly; and
            a knife channel disposed between adjacent rows of the plurality of rows of fastener retaining slots; and a cartridge housing having an arcuate configuration and defining a channel therein configured for receipt of the cartridge assembly, the cartridge housing including:
- a base portion having a concave inner edge and a convex outer edge;
- a first wall extending from the concave inner edge; and
- a second wall extending from the convex outer edge, the first and second walls each defining a plurality of slits therein, wherein each slit of the plurality of slits is spaced from one another along a length of the cartridge housing.

16. The end effector according to claim 15, wherein the first wall has a top surface and a bottom surface and the second wall has a top surface and a bottom surface, wherein each slit of the plurality of slits extends from the top surface of one of the first wall or the second wall to the bottom surface of one of the first wall or the second wall.

17. The end effector according to claim 15, wherein the concave inner edge and the convex outer edge of the base portion defines a plurality of notches therein.

18. The end effector according to claim 15, wherein the cartridge assembly has a concave inner edge and a convex outer edge, at least one of the concave inner edge or the convex outer edge of the cartridge assembly has at least one protrusion, wherein at least one of the first wall or the second wall defines at least one hole therethrough configured for receipt of the at least one protrusion.

19. The end effector according to claim 18, wherein the at least one protrusion is configured for snap fit engagement with the at least one hole.

20. The end effector according to claim 15, wherein the cartridge housing is fabricated from sheet metal.

* * * * *